United States Patent
Krapcho et al.

[11] 3,957,762
[45] May 18, 1976

[54] 2-AMINOALKYL-3,3A,4,5,6,7-HEXAHYDRO-3-PHENYL-7(PHENYLMETHYLENE)-2H-INDAZOLES

[75] Inventors: John Krapcho, Somerset; Chester Frank Turk, Kendall Park, both of N.J.

[73] Assignee: E. R. Squibb & Sons, Inc., Princeton, N.J.

[22] Filed: June 18, 1975

[21] Appl. No.: 588,098

Related U.S. Application Data

[63] Continuation-in-part of Ser. No. 469,171, May 13, 1974, abandoned.

[52] U.S. Cl. ........................ 260/240 D; 260/310 C; 424/273; 260/310 R
[51] Int. Cl.² ............... C07D 231/56; A61K 31/415
[58] Field of Search ................................ 260/240 D

[56] References Cited
UNITED STATES PATENTS
3,852,279  12/1974  Krapcho et al. ................. 260/240 F OTHER PUBLICATIONS
Chemical Abstracts, Vol. 74:53702g (1971).

*Primary Examiner*—Donald B. Moyer
*Attorney, Agent, or Firm*—Lawrence S. Levinson; Merle J. Smith; Stephen B. Davis

[57] ABSTRACT

Compounds of the following formula and their acid addition and quaternary salts and N-oxides

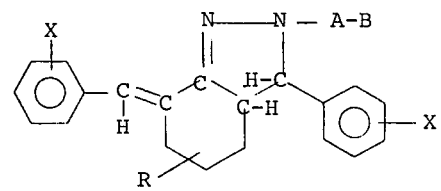

wherein X is hydrogen, chloro, fluoro, trifluoromethyl, lower alkyl, or lower alkoxy, R is hydrogen or lower alkyl, A is alkylene of 1 to 8 carbons, and B is —NH$_2$,

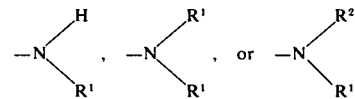

wherein R$^1$ is lower alkyl and R$^2$ is phenyl or phenyl-lower alkyl are disclosed. These compounds are useful as central nervous system depressants.

16 Claims, No Drawings

2-AMINOALKYL-3,3a,4,5,6,7-HEXAHYDRO-3-PHENYL-7(PHENYLMETHYLENE)-2H-INDAZOLES

This application is a continuation-in-part of Ser. No. 469,171 filed on May 13, 1974, now abandoned.

SUMMARY OF THE INVENTION

This invention relates to new compounds of the formula (I)

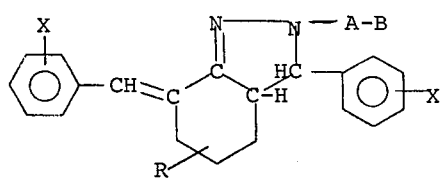

and their acid addition salts, quaternary salts, and N-oxides which are central nervous system depressants.

X represents hydrogen, chloro, fluoro, trifluoromethyl, lower alkyl or lower alkoxy; R represents hydrogen or lower alkyl; A is straight or branched chain alkylene; and B represents —NH$_2$,

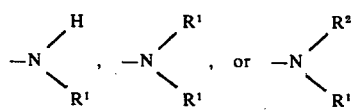

wherein R$^1$ is lower alkyl and R$^2$ is phenyl or phenyl-lower alkyl.

The terms "lower alkyl" and "lower alkoxy" as employed herein include both straight and branched chain radicals of less than eight carbon atoms, preferably 1 to 4 carbon atoms, as for example, methyl, ethyl, propyl, isopropyl, t-butyl, methoxy, ethoxy, propoxy, isopropoxy, n-butoxy, etc. The term "phenyl-lower alkyl" includes such lower alkyl groups attached to a phenyl with benzyl and phenethyl being preferred.

The term "alkylene" as employed herein includes both straight and branched chain radicals of 1 to 8 carbon atoms, as for example, —(CH$_2$)—, —(CH$_2$)$_2$—,

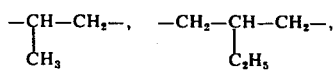

etc.

The term "acid addition salts" is intended to mean salts which may be formed for the purposes of isolation, purification, and storage, such as the oxalate salt, maleate salt, etc. and pharmaceutically acceptable salts meant for administration of the compound to a host, such as the hydrochloride, sulfate, acetate, citrate salts, etc. The quaternary salts include those formed with alkyl halides (e.g. methyl chloride, isobutyl bromide, dodecyl chloride and cetyl iodide), benzyl halides (e.g. benzyl chloride) and dilower alkyl sulfates (e.g. dimethyl sulfate) by a conventional quaternization reaction.

The N-oxide may be formed by dissolving the free base of Formula I in a solvent inert to hydrogen peroxide, e.g., ethanol or chloroform, adding excess (on a molar basis) hydrogen peroxide, and allowing the mixture to stand at room temperature for several hours. An acid-addition salt of the N-oxide may be formed by addition of the desired acid, for example, those mentioned above.

DETAILED DESCRIPTION OF THE INVENTION

The new compounds of formula I are prepared by reacting the appropriate cycloalkylone represented by formula (II)

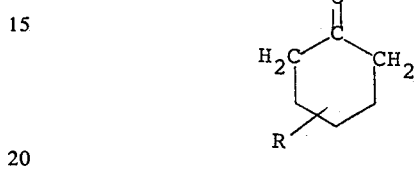

with a substituted benzaldehye of the formula (III)

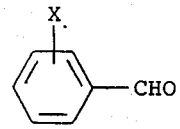

to produce the intermediate of the formula (IV)

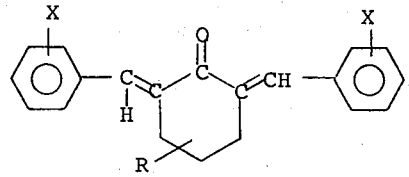

The compounds of formula IV are converted to a compound of formula I by reaction with a hydrazine of the formula (V)

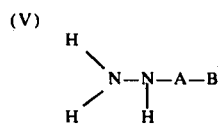

in an organic solvent, preferably an alcohol of up to four carbon atoms at temperatures of from about 40°C to about 120°C, preferably at about the reflux temperature of the solvent, for from about ½ hour to about 12 hours, preferably for about 4 hours.

The hydrazine of formula V is prepared by reacting a haloamine, B-A-halo, with an excess of hydrazine, H$_2$NNH$_2$.

Alternatively, the compound of formula IV can be reacted with a hydroxyalkyl hydrazine of the formula (VI)

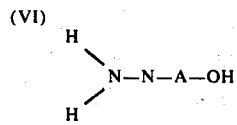

to form the alcohol of the formula (VII)

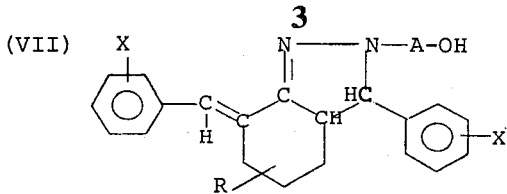

The alcohol of formula VII is reacted by heating with p-toluenesulfonyl chloride to form the tosylate of formula (VIII)

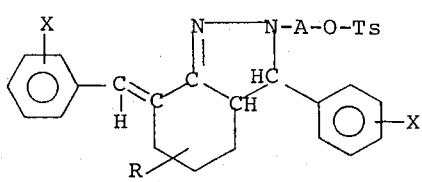

which in turn is treated with the amine of formula HB to form the compounds of formula I. This method is particularly useful in producing compounds of formula I where B is amino (i.e. the tosylate of formula VIII is reacted with ammonia).

Preferred are the compounds of formula I wherein

X is hydrogen, lower alkyl of 1 to 4 carbon atoms, lower alkoxy of 1 to 4 carbon atoms, trifluoromethyl, chloro, or fluoro.

R is hydrogen or lower alkyl of 1 to 4 carbon atoms.

A is straight or branched chain alkylene of from 2 to 5 carbon atoms.

$R^1$ is lower alkyl of 1 to 4 carbon atoms.

$R^2$ is phenyl, benzyl, or phenethyl.

The most preferred compounds are those where

X is hydrogen or Cl, especially hydrogen.

R is hydrogen or t-butyl.

B is

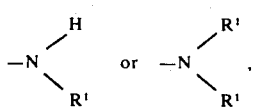

especially

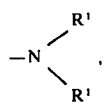

A is —(CH$_2$)$_2$— or —(CH$_2$)$_3$—.

The new compounds of the present invention are useful as central nervous system depressants in mice, cats, rats, dogs and other mammalian species when administered in amounts ranging from about 1.0 mg. to about 100 mg. per kg. of body weight per day. A preferred dosage regimen for optimum results would be from about 10 mg. to about 50 mg. per kg. of body weight per day, and such dosage units are employed that a total of from about 35 mg. to about 3 g. of active ingredient in single or divided doses are administered in a 24 hour period. These compounds when administered to rats in the above stated dosages produced the following central nervous system depressant symptoms; decreased motor activity, ataxia, and decreased screen grip.

For these purposes a compound or mixture of compounds of formula I and their pharmaceutically acceptable acid-addition salts, quaternary salts, or N-oxides may be administered orally or parenterally in a conventional dosage form such as tablet, capsule, injectable or the like. These may be conventionally formulated in an oral or parenteral dosage form by compounding with a conventional vehicle, excipient, binder, preservative, stabilizer, flavor or the like as called for by accepted pharmaceutical practice.

The following examples are illustrative of the invention. All temperatures are expressed on the centigrade scale.

EXAMPLE 1

3,3a,4,5,6,7-Hexahydro-N,N-dimethyl-3-phenyl-7-(phenylmethylene)-2H-indazole-2-propanamine, oxalate salt a. 2,6-Bis(phenylmethylene)cyclohexanone A solution of 32.0 g. (0.33 mole) of cyclohexanone, 70.0 g. (0.66 mole) of benzaldehyde, 200 ml. of ethanol and 20 ml. of concentrated HCl is heated and then refluxed for one hour. Crystallization from the deep red solution occurs and after cooling the crystallized 2,6-bis(phenylmethylene)-cyclohexanone is filtered and washed with cold ethanol and dried yielding 72.0 g.; m.p. 114°–116°. This material is recrystallized from 120 ml. of DMF (dimethylformamide) yielding 56.0 g. (63%) of yellow 2,6-bis(phenylmethylene)cyclohexanone; m.p. 114°–116°.

b. 3,3a,4,5,6,7-Hexahydro-N,N-dimethyl-3-phenyl-7-(phenylmethylene)-2H-indazole-2-propanamine, oxalate salt 11.0 g. (0.04 mole) of 2,6-bis(phenylmethylene)cyclohexanone from part (a) is reacted with 4.8 g. (0.041 mole) of 3-dimethylaminopropyl hydrazine [See Nogrady et al., Can. J. Chem., 47, 2001 (1969)] in 100 ml. of methanol and refluxed for 4 hours. The residue remaining after the evaporation of the methanol is suspended in 100 ml. of water, layered over with 100 ml. of ether, stirred and basified with K$_2$CO$_3$. The layers separate and the aqueous phase is extracted with ether. The combined ether layers are dried (MgSO$_4$) and the solvent is evaporated yielding 14.5 g. of oily base.

A warm solution of 14.0 g. of the oily base in 70 ml. of MeCN is treated with a warm solution of 6.7 g. of oxalic acid in 70 ml. of MeCN. On rubbing and cooling 13.9 g. (75%) of the oxalate salt gradually separates; m.p. 168°–170° (dec.). Crystallization from 25 ml. hot DMF-75 ml. MeCN yields 12.5 g. (68%) of colorless 3,3a,4,5,6,7-hexahydro-N,N-dimethyl-3-phenyl-7-(phenylmethylene)-2H-indazole-2-propanamine, oxalate salt; m.p. 177°–179° (dec.).

EXAMPLE 2

3,3a,4,5,6,7-Hexahydro-N,N-dimethyl-3-(4-chlorophenyl)-7-[(4-chlorophenyl)methylene]-2H-indazole-2-propanamine, hydrochloride salt a. 2,6-Bis[(4-chlorophenyl)methylene]cyclohexanone 32 g. (0.33 mole) of cyclohexanone is reacted with 93 g. (0.66 mole) of 4-chlorobenzaldehyde in 250 ml. of ethanol in the presence of 20 ml. of concentrated HCl as described in part (a) of example 1 to yield 86 g. (77%) of product. Crystallization from 150 ml. of hot dimethylformamide yields 77.9 g. (70%) of yellow solid 2,6-bis[(4-chlorophenyl)methylene]-cyclohexanone; m.p. 142°–144°.

b. 3,3a,4,5,6,7-Hexahydro-N,N-dimethyl-3-(4-chlorophenyl)-7-[(4-chlorophenyl)methylene]-2H-indazole-2-propanamine, hydrochloride salt 17 g. (0.05 mole) of the product from part (a) and 6 g. (0.051 mole) of 3-dimethylaminopropyl hydrazine are reacted in 125 ml. of methanol as described in part (b) of example 1 to yield 21.2 g. of glass-like base. Crystallization from 80 ml. of acetonitrile yields 18.5 g. of pale yellow, 3,3a,4,5,6,7-hexahydro-N,N-dimethyl-3-(4-chlorophenyl)-7-[(4-chlorophenyl)-methylene]-2H-indazole-2-propanamine; m.p. 105°–107°.

A stirred suspension of 18.4 g. of this base in 90 ml. of acetonitrile is treated with 6.1N alcoholic HCl and the resulting solution is diluted to 700 ml. with ether. On rubbing the crystalline salt gradually separates and after cooling for three days 16.8 g. (71%) of crude hydrochloride salt are obtained; m.p. 143°–145° (s. 135°). Crystallization from 80 ml. of methanol-800 ml. of ether yields 12.5 g. (53%) of nearly colorless 3,3a,4,5,6,7-hexahydro-N,N-dimethyl-3-(4-chlorophenyl)-7-[(4-chlorophenyl)methylene]-2H-indazole-2-propanamine, hydrochloride; m.p. 167°–169° (s. 160°).

EXAMPLE 3

3,3a,4,5,6,7-Hexahydro-N,N-dimethyl-3-(4-chlorophenyl)-7-[(4-chlorophenyl)methylene]-2H-indazole-2-propanamine, methanesulfonate salt A mixture of 5.5 g. of 3,3a,4,5,6,7-hexahydro-N,N-dimethyl-3-(4-chlorophenyl)-7-[(4-chlorophenyl)methylene]-2H-indazole-2-propanamine from example 2(b), 1.25 g. of methanesulfonic acid and 40 ml. of acetonitrile is warmed. The resulting solution is then cooled to give 5 g. of a cream-colored solid methanesulfonate salt; m.p. 101°–104° (s. 84°). Recrystallization of 4.9 g. of this salt from 30 ml. of acetonitrile gives 4.0 g. of colorless 3,3a,4,5,6,7-hexahydro-N,N-dimethyl-3-(4-chlorophenyl)-7-[(4-chlorophenyl)methylene]-2H-indazole-2-propanamine, methanesulfonate salt; m.p. 104°–106° (s. 85°).

EXAMPLES 4–11

3,3a,4,5,6,7-Hexahydro-N,N-dimethyl-3-(substituted phenyl)-7-[(substituted-phenyl)methylene]-2H-indazole-2-propanamine, oxalate salts According to the procedure of example 1a, upon substituting in place of the benzaldehyde, one of the following substituted benzaldehydes:
o-chlorobenzaldehyde
m-chlorobenzaldehyde
p-trifluoromethylbenzaldehyde
m-fluorobenzaldehyde
o-methylbenzaldehyde
p-propylbenzaldehyde
m-ethoxybenzaldehyde
p-propoxybenzaldehyde
one obtains the following
2,6-bis[(2-chlorophenyl)methylene]cyclohexanone
2,6-bis[(3-chlorophenyl)methylene]cyclohexanone
2,6-bis[(4-trifluoromethylphenyl)methylene]cyclohexanone
2,6-bis[(3-fluorophenyl)methylene]cyclohexanone
2,6-bis[(2-methylphenyl)methylene]cyclohexanone
2,6-bis[(4-propylphenyl)methylene]cyclohexanone
2,6-bis[(3-ethoxyphenyl)methylene]cyclohexanone
2,6-bis[(4-propoxyphenyl)methylene]cyclohexanone Upon substituting the above compounds in example 1b one obtains the following:
3,3a,4,5,6,7-hexahydro-N,N-dimethyl-3-(2-chlorophenyl)-7-[(2-chlorophenyl)methylene]-2H-indazole-2-propanamine, oxalate salt
3,3a,4,5,6,7-hexahydro-N,N-dimethyl-3-(3-chlorophenyl)-7-[(3-chlorophenyl)methylene]-2H-indazole-2-propanamine, oxalate salt
3,3a,4,5,6,7-hexahydro-N,N-dimethyl-3-(4-trifluoromethylphenyl)-7-[(4-trifluoromethylphenyl)methylene]-2H-indazole-2-propanamine, oxalate salt
3,3a,4,5,6,7-hexahydro-N,N-dimethyl-3-(3-fluorophenyl)-7-[(3-fluorophenyl)methylene]-2H-indazole-2-propanamine, oxalate salt
3,3a,4,5,6,7-hexahydro-N,N-dimethyl-3-(2-methylphenyl)-7-[(2-methylphenyl)methylene]-2H-indazole-2-propanamine, oxalate salt
3,3a,4,5,6,7-hexahydro-N,N-dimethyl-3-(4-propylphenyl)-7-[(4-propylphenyl)methylene]-2H-indazole-2-propanamine, oxalate salt
3,3a,4,5,6,7-hexahydro-N,N-dimethyl-3-(3-ethoxyphenyl)-7-[(3-ethoxyphenyl)methylene]-2H-indazole-2-propanamine, oxalate salt
3,3a,4,5,6,7-hexahydro-N,N-dimethyl-3-(4-propoxyphenyl)-7-[(4-propoxyphenyl)methylene]-2H-indazole-2-propanamine, oxalate salt.

EXAMPLE 12

3,3a,4,5,6,7-Hexahydro-N,N-dimethyl-5-(t-butyl)-3-phenyl-7-(phenylmethylene)-2H-indazole-2-propanamine, maleate salt a. 2,6-Bis(phenylmethylene)-4-t-butylcyclohexanone A suspension of 81.5 g. (0.5 mole) of 4-t-butylcyclohexanone in 250 ml. of ethanol is stirred, treated with 110 g. (1.03 mole) of benzaldehyde, and then treated with 30 ml. of concentrated HCl. The resulting yellow solution is refluxed for three hours, cooled, and an orange colored solid is filtered and air dried to give 212 g. of crude product; m.p. 134°–136°. This crude product is crystallized from 900 ml. of acetonitrile to give 137 g. of yellow-orange product; m.p. 137°–139°. This material is dissolved in 400 ml. of hot ethyl acetate and the resulting solution is diluted with 400 ml. of warm ethanol. This solution is allowed to cool to room temperature and a pale yellow solid is filtered and dried to yield 107.3 g. of 2,6-bis(phenylmethylene)-4-t-butylcyclohexanone; m.p. 139°–141°.

b. 3,3a,4,5,6,7-Hexahydro-N,N-dimethyl-5-(t-butyl)-3-phenyl-7-(phenylmethylene)-2H-indazole-2-propanamine, maleate salt 16.5 g. (0.05 mole) of the 2,6-bis(phenylmethylene)-4-t-butylcyclohexanone and 5.9 (0.05 mole) of 3-dimethylaminopropyl hydrazine are reacted in 125 ml. of methanol as described in Example 1(b) to give 20.9 g. of oil base. This material is dissolved in 100 ml. of warm acetonitrile and treated with a warm solution of 4.4 g. of oxalic acid in 50 ml. of acetonitrile. On cooling and rubbing, 14.7 g. of crude oxalate salt slowly separates. This material is crystallized from 50 ml. of acetonitrile and recrystallized from 50 ml. of isopropyl alcohol to give 9.2 g. of cream colored 3,3a,4,5,6,7-hexahydro-N,N-dimethyl-5-(t-butyl)-3-phenyl-7-(phenylmethylene)-2H-indazole-2-propanamine, oxalate salt.

This oxalate is treated with K₂CO₃ and extracted with ether to yield 7.0 g. of glass-like base. This base and 1.9 g. of maleic acid are dissolved in 40 ml. of warm acetonitrile and diluted to approximately 300 ml. with ether. On rubbing and cooling, 8.0 g. of crude maleate salt separates. Crystallization from 50 ml. of warm methanol and 300 ml. of ether gives 7.3 g. of colorless 3,3a,4,5,6,7-hexahydro-N,N-dimethyl-5-(t-butyl)-3-phenyl-7-(phenylmethylene)-2H-indazole-2-propanamine, maleate salt; m.p. 169°–171°.

EXAMPLES 13–18

3,3a,4,5,6,7-Hexahydro-N,N-dimethyl-3-(phenyl)-(5 or 4 and/or 6-lower alkyl)-7-(phenylmethylene)-2H-indazole-2-propanamine, oxalate salts According to the procedure of example 1a, upon substituting in place of the cyclohexanone, one of the following:

p-methylcyclohexanone
p-ethylcyclohexanone
p-propylcyclohexanone
p-n-butylcyclohexanone
m-methylcyclohexanone
m-ethylcyclohexanone one obtains the following:

2,6-bis(phenylmethylene) (4-methylcyclohexanone)
2,6-bis(phenylmethylene) (4-ethylcyclohexanone)
2,6-bis(phenylmethylene) (4-propylcyclohexanone)
2,6-bis(phenylmethylene) (4-n-butylcyclohexanone)
2,6-bis(phenylmethylene) (3-methylcyclohexanone)
2,6-bis(phenylmethylene) (3-ethylcyclohexanone)

Upon substituting the above compounds in example 12 one obtains the following:

3,3a,4,5,6,7-hexahydro-N,N-dimethyl-5-methyl-3-phenyl-7-(phenylmethylene)-2H-indazole-2-propanamine, maleate salt 3,3a,4,5,6,7-hexahydro-N,N-dimethyl-5-ethyl-3-phenyl-7-(phenylmethylene)-2H-indazole-2-propanamine, maleate salt 3,3a,4,5,6,7-hexahydro-N,N-dimethyl-3-phenyl-5-propyl-7-(phenylmethylene)-2H-indazole-2-propanamine, maleate salt 3,3a,4,5,6,7-hexahydro-N,N-dimethyl-5-(n-butyl)-3-phenyl-7-(phenylmethylene)-2H-indazole-2-propanamine, maleate salt 3,3a,4,5,6,7-hexahydro-N,N-dimethyl-(4 and/or 6-methyl)-3-phenyl-7-(phenylmethylene)-2H-indazole-2-propanamine, maleate salt; and 3,3a,4,5,6,7-hexahydro-N,N-dimethyl-(4 and/or 6-ethyl)-3-phenyl-7-(phenylmethylene)-2H-indazole-2-propanamine, maleate salt.

Similarly, by employing the substituted benzaldehydes of examples 2 and 4–11 within the procedure of examples 12–18, other compounds within the scope of the invention are obtained.

EXAMPLE 19

3,3a,4,5,6,7-Hexahydro-N,N-dimethyl-3-phenyl-7-(phenylmethylene)-2H-indazole-2-ethanamine, maleate salt Following the procedure of example 1 but substituting 2-dimethylaminoethyl hydrazine for the 3-dimethylaminopropyl hydrazine in part (b), one obtains 3,3a,4,5,6,7-hexahydro-N,N-dimethyl-3-phenyl-7-(phenylmethylene)-2H-indazole-2-ethanamine, oxalate salt (crystallized from ethanol-methanol); m.p. 157°–159°.

This oxalate is converted to the free base and then to the maleic acid salt as taught in example 12(b) to yield 3,3a,4,5,6,7-hexahydro-N,N-dimethyl-3-phenyl-7-(phenylmethylene)-2H-indazole-2-ethanamine, maleate salt (crystallized from methanolether); m.p. 137°–139°.

EXAMPLE 20

3,3a,4,5,6,7,-Hexahydro-N,N-diethyl-3-phenyl-7-(phenylmethylene)-2H-indazole-2-propanamine, maleate salt Following the procedure of example 1 but substituting 3-diethylaminopropyl hydrazine for the 3-dimethylaminopropyl hydrazine, one obtains colorless crystals of 3,3a,4,5,6,7-hexahydro-N,N-diethyl-3-phenyl-7-(phenylmethylene)-2H-indazole-2-propanamine, oxalate salt (crystallized from dimethylformamideacetonitrile); m.p. 145°–147°.

This oxalate salt is converted to the free base and then to the maleic acid salt as set forth in example 12 (b). Crystallization from methanol-ether yields nearly colorless 3,3a,4,5,6,7-hexahydro-N,N-diethyl-3-phenyl-7-(phenylmethylene)-2H-indazole-2-propanamine, maleate salt; m.p. 104°–106°.

EXAMPLES 21–34

Following the procedure of example 1 but substituting the hydrazine shown in column A for the 3-dimethylaminopropylhydrazine the products shown in column B are obtained.

| Ex. | Col. A | Col. B |
|---|---|---|
| 21 | 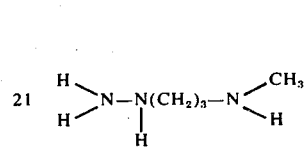 | 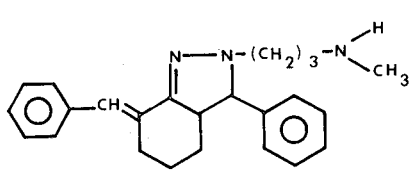 |
| 22 | 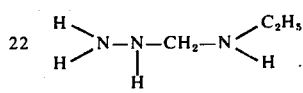 | 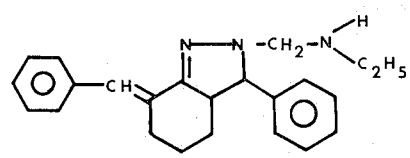 |

| Ex. | Col. A | Col. B |
|---|---|---|
| 23 | 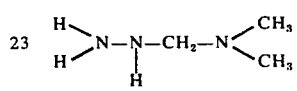 | 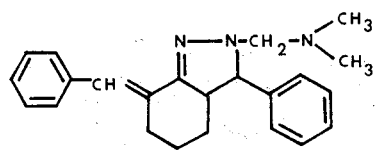 |
| 24 | 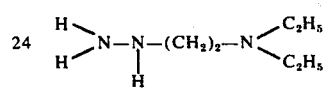 | 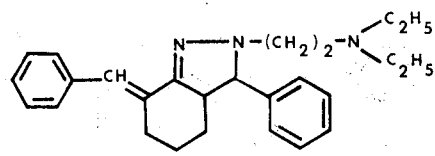 |
| 25 | 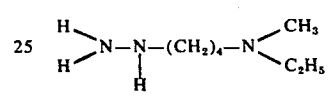 | 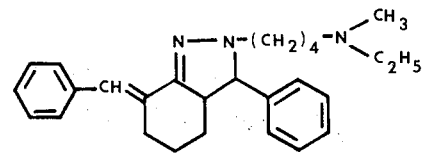 |
| 26 | 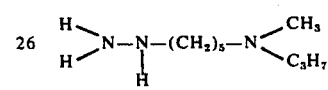 | 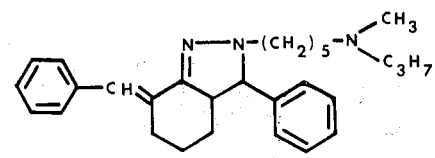 |
| 27 | 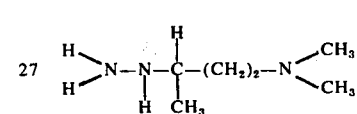 | 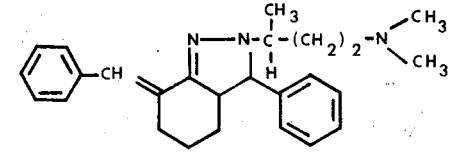 |
| 28 | 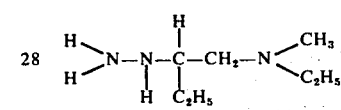 | 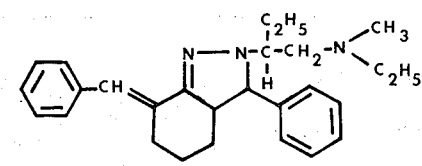 |
| 29 | 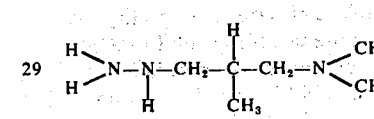 | 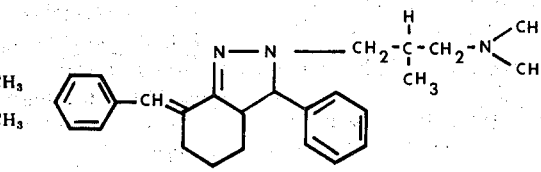 |

| Ex. | Col. A | Col. B |
|---|---|---|
| 30 | 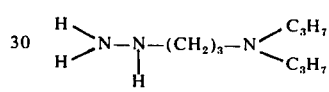 | 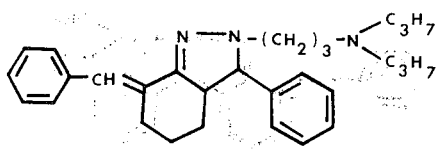 |
| 31 | 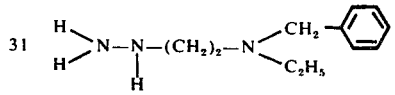 | 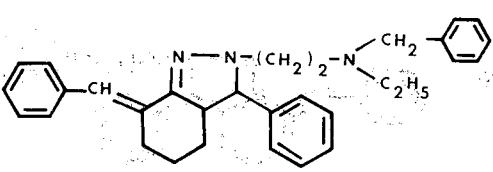 |
| 32 | 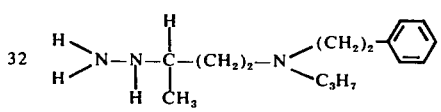 | 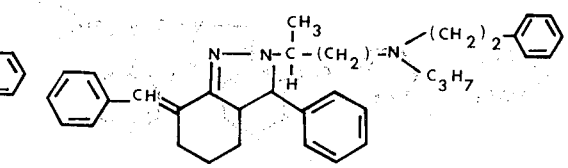 |
| 33 | 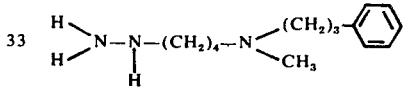 | 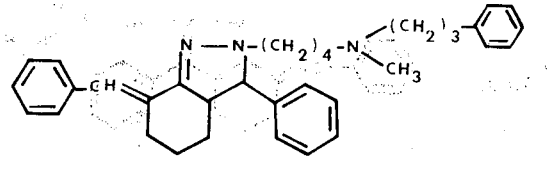 |
| 34 | 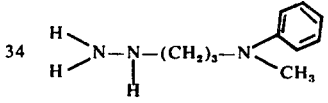 | 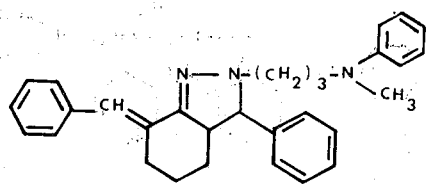 |

Similarly, the hydrazines shown in column A of examples 21–34 can be employed in the procedures of examples 2–20 to prepare other compounds within the scope of this invention.

EXAMPLE 35

3,3a,4,5,6,7-Hexahydro-3-phenyl-7-(phenylmethylene)-2H-indazole-2-ethanamine, oxalate salt a. 3,3a,4,5,6,7-Hexahydro-3-phenyl-7-(phenylmethylene)-2-H-indazole-2-ethanol A suspension of the 2,6-bis(phenylmethylene)cyclohexanone from example 1a in methanol is treated with (2-hydroxyethyl)hydrazine. The mixture is heated and the resulting solution is refluxed for four hours, cooled, and the bulk of the methanol is evaporated. The resulting alcohol is triturated with ether, cooled overnight, filtered, and dried in vacuo.

b. 3,3a,4,5,6,7-Hexahydro-3-phenyl-7-(phenylmethylene)-2H-indazole-2-ethanamine, oxalate salt The alcohol from part (a) is converted to the tosylate by treatment with p-toluenesulfonyl chloride in pyridine. The tosylate is reacted with ammonia and treated with a solution of oxalic acid in MeCN as described in example 1b yielding 3,3a,4,5,6,7-hexahydro-3-7-

(phenylmethylene)-2H-indazole-2-ethanamine, oxalate salt.

EXAMPLES 36–39

Following the procedure of example 35 but substituting the following alkylamines for the ammonia
methylamine
ethylamine
n-propylamine
t-butylamine one obtains the following:

3,3a,4,5,6,7-hexahydro-N-methyl-3-phenyl-7-(phenylmethylene)-2H-indazole-2-ethanamine, oxalate salt, 3,3a,4,5,6,7-hexahydro-N-ethyl-3-phenyl-7-(phenylmethylene)-2H-indazole-2-ethanamine, oxalate salt, 3,3a,4,5,6,7-hexahydro-N-n-propyl-3-phenyl-7-(phenylmethylene)-2H-indazole-2-ethanamine, oxalate salt, and 3,3a,4,5,6,7-hexahydro-N-t-butyl-3-phenyl-7-(phenylmethylene)-2H-indazole-2-ethanamine, oxalate salt.

Similarly, the process of examples 35–39 can be employed to prepare the compounds of examples 1–34.

EXAMPLE 40

3,3a,4,5,6,7-Hexahydro-N,N-dimethyl-3-phenyl-7-(phenylmethylene)-2H-indazole-2-propanamine, methochloride The oxalate salt of example 1 is basified by treatment with $K_2CO_3$. A solution of the base in MeCN is cooled and treated with methyl chloride. The solution is allowed to stand for one day and the solvent is evaporated to give 3,3a,4,5,6,7-hexahydro-N,N-dimethyl-3-phenyl-7-(phenylmethylene)-2H-indazole-2-propanamine, methochloride.

EXAMPLE 41

3,3a,4,5,6,7-Hexahydro-N,N-dimethyl-3-phenyl-7-(phenylmethylene)-2H-indazole-2-propanamine, N-oxide A solution of the free base of example 1 in methanol is treated with two equivalents of 30% $H_2O_2$. The solution is allowed to stand for two days and the solvent is removed under reduced pressure to give 3,3a,4,5,6,7-hexahydro-N,N-dimethyl-3-phenyl-7-(phenylmethylene)-2H-indazole-2-propanamine, N-oxide.

What is claimed is:

1. A compound of the formula:

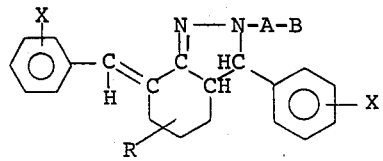

wherein X is selected from the group consisting of hydrogen, chloro, fluoro, lower alkyl of 1 to 4 carbons, lower alkoxy of 1 to 4 carbons, and trifluoromethyl; R is selected from the group consisting of hydrogen and lower alkyl of 1 to 4 carbons; A is straight or branched chain alkylene of 1 to 8 carbons; B is selected from the group consisting of —$NH_2$,

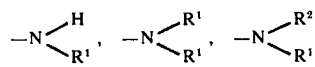

wherein $R^1$ is lower alkyl of 1 to 4 carbons and $R^2$ is phenyl, benzyl, or phenethyl; and an acid addition or quaternary salt or N-oxide thereof.

2. The compound of claim 1 wherein A is straight or branched chain alkylene of 2 to 5 carbon atoms.

3. The compound of claim 2 wherein A is —$(CH_2)_2$— or —$(CH_2)_3$—; X is hydrogen or chloro; and B is

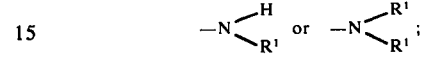

and R is hydrogen or t-butyl.

4. The compound of claim 3 wherein X is hydrogen and B is

5. The compound of claim 4 wherein A is —$(CH_2)_2$—; each $R^1$ is $CH_3$; and R is hydrogen.

6. The compound of claim 5 having the name 3,3a,4,5,6,7-hexahydro-N,N-dimethyl-3-phenyl-7-(phenylmethylene)-2H-indazole-2-ethanamine, maleate salt.

7. The compound of claim 4 wherein A is —$(CH_2)_3$—; each $R^1$ is $CH_3$; and R is hydrogen.

8. The compound of claim 7 having the name 3,3a,4,5,6,7-hexahydro-N,N-dimethyl-3-phenyl-7-(phenylmethylene)-2H-indazole-2-propanamine, oxalate salt.

9. The compound of claim 4 wherein A is —$(CH_2)_3$—; each $R^1$ is $C_2H_5$; and R is hydrogen.

10. The compound of claim 9 having the name 3,3a,4,5,6,7-hexahydro-N,N-diethyl-3-phenyl-7-(phenylmethylene)-2H-indazole-2-propanamine, maleate salt.

11. The compound of claim 4 wherein A is —$(CH_2)_3$—; each $R^1$ is $CH_3$; and R is t-butyl.

12. The compound of claim 11 having the name 3,3a,4,5,6,7-hexahydro-N,N-dimethyl-5-(t-butyl)-3-phenyl-7-(phenylmethylene)-2H-indazole-2-propanamine, maleate salt.

13. The compound of claim 3 wherein X is chloro and B is

14. The compound of claim 13 wherein A is —$(CH_2)_3$—; each $R^1$ is $CH_3$; and R is hydrogen.

15. The compound of claim 14 having the name 3,3a,4,5,6,7-hexahydro-N,N-dimethyl-3-(4-chlorophenyl)-7-[(4-chlorophenyl)-methylene]-2H-indazole-2-propanamine, hydrochloride salt.

16. The compound of claim 14 having the name 3,3a,4,5,6,7-hexahydro-N,N-dimethyl-3-(4-chlorophenyl)-7-[(4-chlorophenyl)-methylene]-2H-indazole-2-propanamine, methanesulfonate salt.

* * * * *